United States Patent [19]

Kazama

[11] Patent Number: 4,776,426
[45] Date of Patent: Oct. 11, 1988

[54] STETHOSCOPE

[76] Inventor: Shigeru Kazama, 6-3, Naruse 2-chome, Machida-shi, Tokyo, Japan

[21] Appl. No.: 831,351

[22] Filed: Feb. 20, 1986

[30] Foreign Application Priority Data

May 31, 1985 [JP] Japan ............................. 60-81075[U]

[51] Int. Cl.⁴ ................................................ A61B 7/02
[52] U.S. Cl. ..................................... 181/131; 181/137
[58] Field of Search .................................. 181/137, 131

[56] References Cited

U.S. PATENT DOCUMENTS 3,144,091 8/1964 Bodenger ............................ 181/137
3,938,615 2/1976 Bodenger ......................... 181/137 X
4,212,368 7/1980 Allen ................................ 181/137 X

FOREIGN PATENT DOCUMENTS 1267378 5/1968 Fed. Rep. of Germany ...... 181/137
1504079 3/1978 United Kingdom ................ 181/137

Primary Examiner—Benjamin R. Fuller
Attorney, Agent, or Firm—Bierman & Muserlian

[57] ABSTRACT

A stethoscope consisting of a pair of flexible ear tubes and a chest piece divided by a partition into two sound receiving chambers. These chambers are separately communicated with the right and left ear tubes, respectively.

1 Claim, 3 Drawing Sheets

STETHOSCOPE

BACKGROUND OF THE INVENTION

This invention relates to stethoscopes, and more particularly to a stethoscope consisting of a pair of ear tubes and a chest piece which can receive sounds at two different locations adjacent to each other of a human body.

In medical auscultation, when sound produced in a human body, such as respiratory, cardiac, pleural, or other sound, is caught from two locations adjacent to each other of the body, there is difference between the sound vibrations. It is important to know simultaneously the difference between the two in exact medical diagnosis.

Conventionally, a stethoscope consists of a chest piece or bell having a single sound receiving chamber therein and a pair of auscultatory tubes, i.e., right and left ear tubes connected to the bell. In auscultation by means of the conventional stethoscope mentioned above, the both ears of the observer only can catch the same sound vibration from the chest piece at the same time.

When the usual stethoscope with a single sound receiving chamber therein is used, therefore, it is impossible to hear and recognize the difference between the sound vibrations at two locations adjacent to each other of the human body simultaneously.

A stethoscope of the type having a plurality of microphones in a single body, such as a dual microphone which is the conventional structure having, for example, a bell-shaped microphone diametrically opposed to a diaphragm-type microphone in a single body is already well known in the art. Even by means of the dual microphone type stethoscope, however, the observer cannot recognize the difference between the sound vibrations at two different locations of the human body at the same time.

It has previously been proposed to hear sound at two different locations of a patient body separately by a stethoscope. The above proposed stethoscope consists of a pair of chest pieces and a pair of ear tubes connected with the respective chest pieces. Consequently, in medical auscultation by means of the proposed stethoscope, both ears of the observer can catch the sound vibrations from two different locations of the body at the same time, separately. The pair of chest pieces, however, must be held in the respective hands of the observer. This is too much trouble and inconvenient to examine a patient body.

OBJECTS OF THE INVENTION

In view of the foregoing, it is an object of the present invention to provide a stethoscope which can receive sound vibrations from two different locations adjacent to each other of a patient body, and can also transmit individual sound vibration to the respective ears of the observer, simultaneously, even if the source of sound is in one portion within the body.

It is a further object of the present invention to provide a stethoscope with a chest piece which is divided by a partition into two sound receiving chambers and is well adapted to hold in one hand.

It is another object of the present invention to provide an improved stethoscope of simple inexpensive design.

BRIEF DESCRIPTION OF THE DRAWINGS

The above and other objects, features and advantages of the present invention will be more clearly understood when considered in conjunction with the following description and accompanying drawings, in which.

DESCRIPTION OF THE PREFERRED EMBODIMENTS

Figure 1:
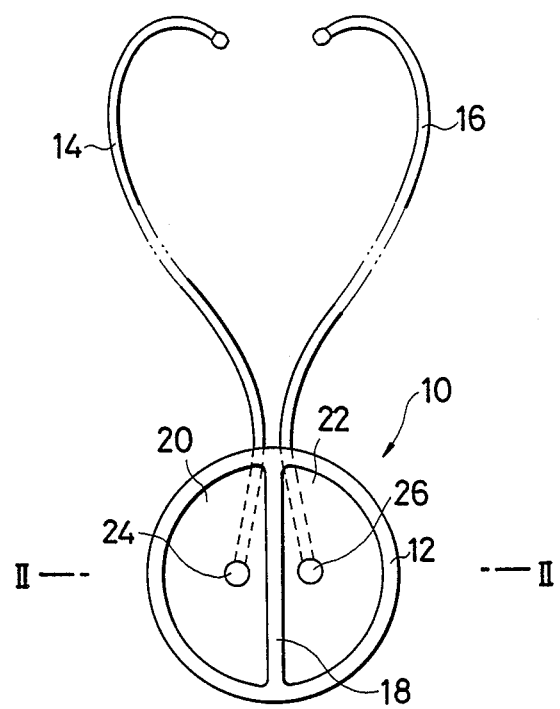
FIG. 1 is a schematic representation of the first embodiment of the stethoscope of the present invention.
Figure 2:
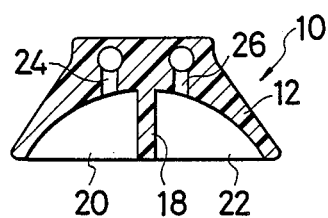
FIG. 2 is a cross sectional view taken on line II—II of FIG. 1.

Referring now in particular to the drawings, wherein like reference characters designate like or corresponding parts throughout.

In the first embodiment of the present invention as illustrated in FIG. 1, a stethoscope generally designated 10 consists of a bell shaped microphone body 12 and a pair of flexible ear tubes 14 and 16. The microphone body 12 is divided into a pair of semicircular sound receiving chambers 20 and 22 by means of a central partition 18. At the apex of each of the sound receiving chambers 20 and 22, an opening 24 or 26 is formed therein. One end of the ear tube 14 is inserted into the opening 24 and one end of the other ear tube 16 is inserted into the opening 26.

Figure 3:
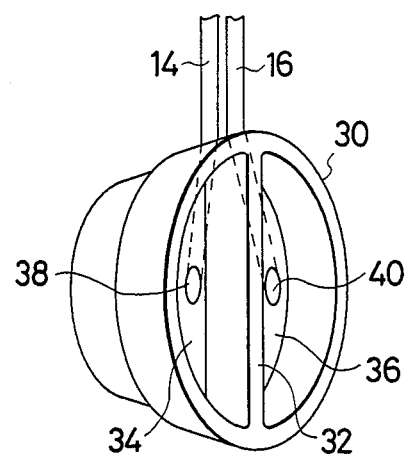
FIG. 3 is a perspective view of a chest piece body of the second embodiment of the present invention.
Figure 4:
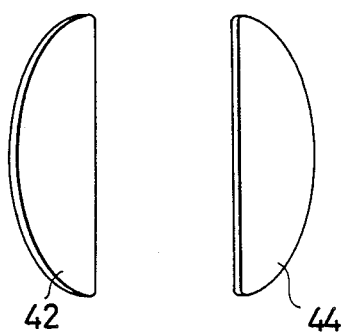
FIG. 4 is a perspective view of a pair of diaphragms to be assembled in the second embodiment of the stethoscope.
Figure 5:
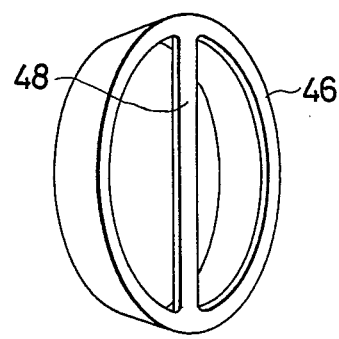
FIG. 5 is a perspective view of a frame to secure the diaphragms to the chest piece body.

Referring to FIG. 3 through FIG. 5, there are shown the second embodiment of the present invention, in which the chest piece is illustrated as a diaphragm type microphone. The body 30 of the microphone is divided into a pair of semicircular sound receiving chambers 34 and 36 by a central partition 32. Openings 38 and 40 are respectively formed at the apex of each of the sound receiving chambers 34 and 36. One end of the flexible ear tube 14 is connected with the opening 38 and one end of the flexible tube 16 is connected with the opening 40. A pair of semicircular diaphragms 42 and 44 (FIG. 4) are respectively mounted on the open end of the respective semicircular sound receiving chambers 34 and 36. These diaphragms 42 and 44 are secured to the body 30 by means of a circular frame 46 (FIG. 5). If desired, the frame 46 may be provided with a central frame portion 48, as shown in FIG. 5, so as to align with the partition 32 and to support the periphery of each of the diaphragms 42 and 44 between the central partition 32 and the central frame portion 48.

Figure 6:
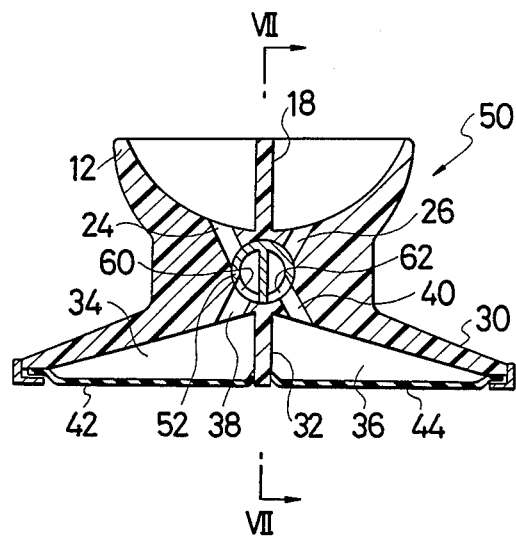
FIG. 6 is a cross sectional view of the third embodiment of the stethoscope according to the present invention.
Figure 7:
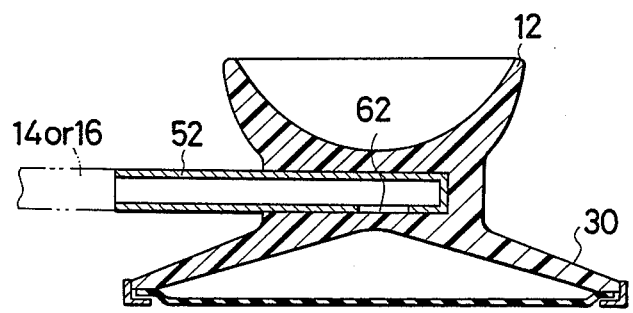
FIG. 7 is a cross sectional view taken in the direction of the arrows substantially along line VII—VII of FIG. 6.
Figure 8:
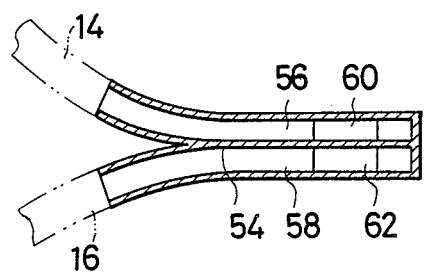
FIG. 8 is a cross section of a tubular shaft to be assembled in the third embodiment of the present invention.

With reference to FIGS. 6, 7 and 8, the third embodiment of the stethoscope according to the present invention will be explained in detail. In this embodiment, a chest piece 50 has a bell shaped microphone body 12 with the central partition 18 of the first embodiment of the invention diametrically opposed to a diaphragm microphone body 30 with the central partition 32 and the diaphragms 42 and 44 of the second embodiment of the invention in a single body. As shown in FIGS. 6 and 7, between the bell shaped microphone body 12 and the diaphragm microphone body 30 a cylindrical recess is formed to receive a tubular shaft 52 therein. The tubular shaft 52 is divided by a central partition 54 into a pair of passages 56 and 58. One end of the ear tube 14 is connected to the passage 56 and one end of the ear tube 16 is connected to the passage 58. To this end, the tubular shaft 52 may be preferably formed in Y-shaped configuration, as shown in FIG. 8. In a side wall of the portion of each of the passages 56 and 58 is provided with a hole 60 or 62 which can be selectively aligned and communicated with either respective openings 24 and 26 in the bell shaped microphone 12 or respective openings 38 and 40 in the diaphragm microphone 30 by rotating the tubular shaft 52 in the cylindrical recess.

According to the stethoscope of the present invention, in medical auscultation, the observer can manipulate the chest piece in one hand and his right ear can hear the sound caught by the right sound receiving chamber of the chest piece while his left ear will hear the sound caught by the other at the same time so that it provides a stereophonic effect and more sensitive reception in order to determine exactly the condition of the locations beneath the pitch, loudness, character or realistic spread of the sound.

While certain preferred embodiments of the invention have been described, it is to be understood that modifications will be apparent to those skilled in the art without departing from the spirit of the invention.

The scope of the invention, therefore, is to be determined solely by the following claims.

I claim:

1. A stethoscope comprising a pair of flexible ear tubes and a chest piece having an open-bell type microphone and a diaphragm type microphone, said open-bell type microphone having a central chamber divided by a central partition into two symmetrical semicircular sound chambers, said central partition having a height the same as a rim of outer openings of said semicircular sound chambers, each of said sound chambers being provided with an inner opening adjacent to said central partition, said diaphragm type microphone having a central chamber divided by a central partition into two symmetrical semicircular sound receiving chambers, said central partition having a height the same as a rim of outer openings of said semicircular sound chambers, and each of the outer openings of said sound chambers being covered with a semicircular diaphragm, each of said diaphragm-covered semicircular sound chambers being provided with an inner opening adjacent to said central partition, and said pair of ear tubes selectively communicating with either said open-bell type microphone or said diaphragm type microphone through said inner openings.

* * * * *